United States Patent
Brady

(10) Patent No.: US 12,256,918 B2
(45) Date of Patent: Mar. 25, 2025

(54) INSERTER ASSEMBLY WITH SUTURE PROTECTOR TUBING AND METHOD OF USE

(71) Applicant: Arthrex, Inc., Naples, FL (US)

(72) Inventor: Paul C. Brady, Knoxville, TN (US)

(73) Assignee: Arthrex, Inc., Naples, FL (US)

( * ) Notice: Subject to any disclaimer, the term of this patent is extended or adjusted under 35 U.S.C. 154(b) by 930 days.

(21) Appl. No.: 16/737,066

(22) Filed: Jan. 8, 2020

(65) Prior Publication Data
US 2021/0204931 A1   Jul. 8, 2021

(51) Int. Cl.
*A61B 17/04*     (2006.01)
*A61F 2/08*      (2006.01)

(52) U.S. Cl.
CPC .. *A61B 17/0401* (2013.01); *A61B 2017/0409* (2013.01); *A61B 2017/044* (2013.01); *A61F 2002/0852* (2013.01)

(58) Field of Classification Search
CPC ........ A61B 17/0401; A61B 2017/0409; A61B 2017/044; A61F 2/0811; A61F 2002/0817; A61F 2002/0847–0888
See application file for complete search history.

(56) References Cited

U.S. PATENT DOCUMENTS

| | | |
|---|---|---|
| 5,718,717 A | 2/1998 | Bonutti |
| 5,980,559 A | 11/1999 | Bonutti |
| 6,572,635 B1 | 6/2003 | Bonutti |
| 6,616,663 B2 | 9/2003 | Glenn et al. |
| 6,955,683 B2 | 10/2005 | Bonutti |
| 8,845,687 B2 | 9/2014 | Bonutti |
| 2002/0188301 A1 | 12/2002 | Dallara et al. |
| 2003/0135239 A1* | 7/2003 | Gabriel ............. A61B 17/0401 606/232 |
| 2012/0029562 A1* | 2/2012 | Trenhaile .......... A61B 17/0401 606/232 |
| 2013/0006276 A1* | 1/2013 | Lantz .................... A61B 90/03 606/144 |
| 2019/0090868 A1* | 3/2019 | Bracy ................ A61B 17/0482 |
| 2020/0253598 A1* | 8/2020 | Holmes, Jr. ........ A61B 17/0401 |

FOREIGN PATENT DOCUMENTS

| | | |
|---|---|---|
| WO | WO 1990/009149 | 8/1990 |
| WO | WO 2017/011014 A1 | 1/2017 |

* cited by examiner

*Primary Examiner* — Elizabeth Houston
*Assistant Examiner* — Lindsey Bachman
(74) *Attorney, Agent, or Firm* — Blank Rome LLP

(57) ABSTRACT

A surgical inserter assembly for implanting a suture anchor into bone. The assembly includes an outer protector tube that prevents the anchored suture from being damaged by the instruments used during surgery. The outer protector tube remains in place around the suture after the suture anchor is installed.

20 Claims, 3 Drawing Sheets

INSERTER ASSEMBLY WITH SUTURE PROTECTOR TUBING AND METHOD OF USE

BACKGROUND OF THE INVENTION

1. Field of the Invention

The present disclosure generally relates to an inserter assembly and method for use in surgical tissue repair that provides protection to the repair sutures.

2. Description of the Related Art

When soft tissue, such as a ligament or a tendon, becomes detached from a bone, surgery is usually required to reattach or reconstruct the tissue. A tissue graft may be used that attaches to the bone to facilitate regrowth and permanent attachment. Known techniques and devices for reattaching tissue involve tying down the soft tissue against the bone using a suture anchor, i.e., a suture attached to an anchor which can be inserted into a hole drilled in the bone for tissue fixation thereto.

Once the anchor is implanted in the bone hole and the inserter removed, treatment of the surrounding tissue is often required to complete the repair. For example, in an arthroscopy procedure, after the anchor and suture is inserted in bone, the arthroscopic camera is usually repositioned into the sub-acromial space so that the surrounding tissue can be debrided. The surgeon clears out the surrounding tissue with a radio frequency wand or a tissue shaver, which often results in damage to the exposed suture.

Therefore, a need exists for protecting the sutures of anchor from being damaged by the instruments used during surgery, and particularly for tissue debridement.

SUMMARY OF THE INVENTION

Accordingly, the present invention provides a surgical inserter assembly that comprises a fixation device configured for fixation in bone, that has proximal and distal ends, and that is pre-loaded with a flexible strand. The assembly comprises an inserter that has a cannulated shaft with a fixation device engagement end configured to engage the proximal end of the fixation device, with the flexible strand extending through the cannulated shaft. An outer protector tube slidably receives the cannulated shaft of the inserter such that the inserter is removable from the outer protector tube while leaving the flexible strand extending through the outer protector tube.

Preferably, the inner diameter of the outer protector tube is smaller than the outer diameter of the proximal end of the fixation device, such that no portion of the fixation device is received in the outer protector tube; the outer protector tube is positioned between the handle of the cannulated shaft of the inserter and the proximal end of the fixation device; the outer protector tube is axially fixed in place between the handle and the fixation device; the outer protector tube covers substantially the entire length of the cannulated shaft; the outer protector tube is made of plastic or a plastic composite; the fixation device has outer threads configured to anchor into the bone hole, tunnel, or other crevice; the flexible strand is a suture or suture tape; and the flexible strand is coupled to the distal end of the fixation device via a knot.

The present invention also includes a method of use of a surgical inserter assembly, comprising the steps of positioning an outer protector tube over the cannulated shaft of the inserter of the inserter assembly; engaging the end of the cannulated shaft of the inserter with a fixation device; installing the fixation device, using the inserter, in a bone hole, tunnel, or other crevice, the fixation device being pre-loaded with a least one flexible strand; and after installing the fixation device, disengaging the inserter from the fixation device and removing the inserter from the outer protector tube, thereby leaving the fixation device in the bone hole, tunnel, or other crevice, and leaving the flexible strand inside of the outer protector tube.

Preferably, the outer protector tube remains stationary while removing the inserter; movement of the outer protector tube is restricted by a handle end of the inserter and the proximal end of the fixation device when installing the fixation device; the method further comprises the step of extending the flexible strand through the cannulated shaft of the inserter after positioning the outer protector tube over the cannulated shaft and before the step of installing the fixation device; the flexible strand extends through the outer protector tube after the inserter is removed; once the flexible strand is extended through the cannulated shaft of the inserter, the outer protector tube is fixed in place between a handle of the inserter assembly and the proximal end of the fixation device; the method further comprises the step of removing the handle before the step of removing the inserter from the outer protector tube; the step of installing the fixation device includes anchoring the fixation device by threading the fixation device into the bone hole, tunnel, or other bone crevice; the method further comprises the step of pre-drilling the bone hole, tunnel, or other bone crevice prior to the step of installing the fixation device; the outer protector tube remains in place after removal of the inserter and during subsequent tissue preparation; and the inner diameter of the outer protector tube is less than the outer diameter of the proximal end of the fixation device, such that no portion of the outer protector tube is inserted into the bone hole, tunnel, or other bone crevice.

DETAILED DESCRIPTION OF THE PREFERRED EMBODIMENTS

Figure 1:
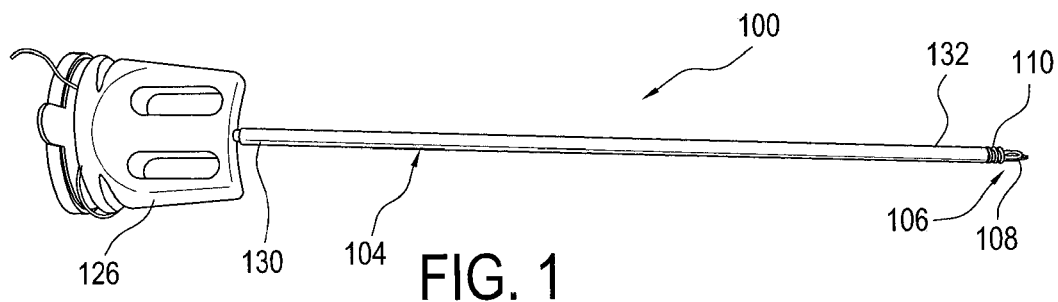
FIG. 1 is a plan view of a surgical inserter assembly according to an exemplary embodiment.

Referring to the figures, in general, the present disclosure relates to a surgical inserter assembly 100 and method for use in surgical tissue repair procedures designed to provide protection to the repair sutures during the procedure.

As seen in FIGS. 2a-2e, the surgical inserter assembly 100 generally comprises an inserter 102, an outer protector tube 104, and a fixation device 106 that can be pre-loaded with one more flexible strands 20. The fixation device 106 has distal and proximal ends 108 and 110, an inner bore 112 therebetween, and an outer fixation surface 114, such as outer threads, for anchoring the fixation device 106 to the inner surface of a bone hole 90 (FIGS. 3a and 3b), tunnel, or other crevice in the bone. Fixation device 106 may be any device suitable for anchoring suture into a bone hole, tunnel, or other crevice.

Figure 3A:
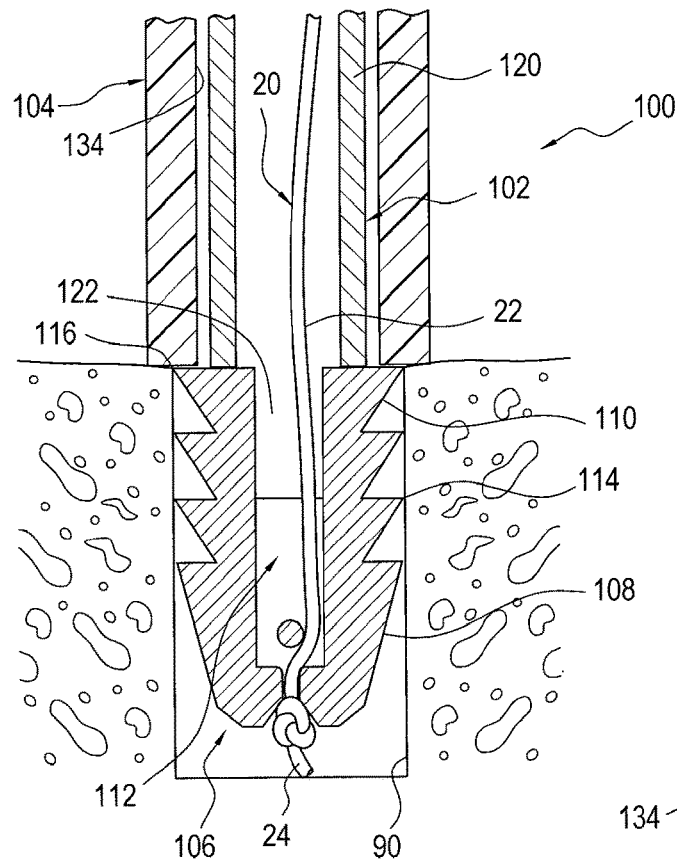
FIGS. 3*a* and 3*b* are cross-sectional views of the surgical inserter assembly illustrated in FIG. 1, showing the use of the surgical inserter assembly to install the fixation device in bone.
Figure 3B:
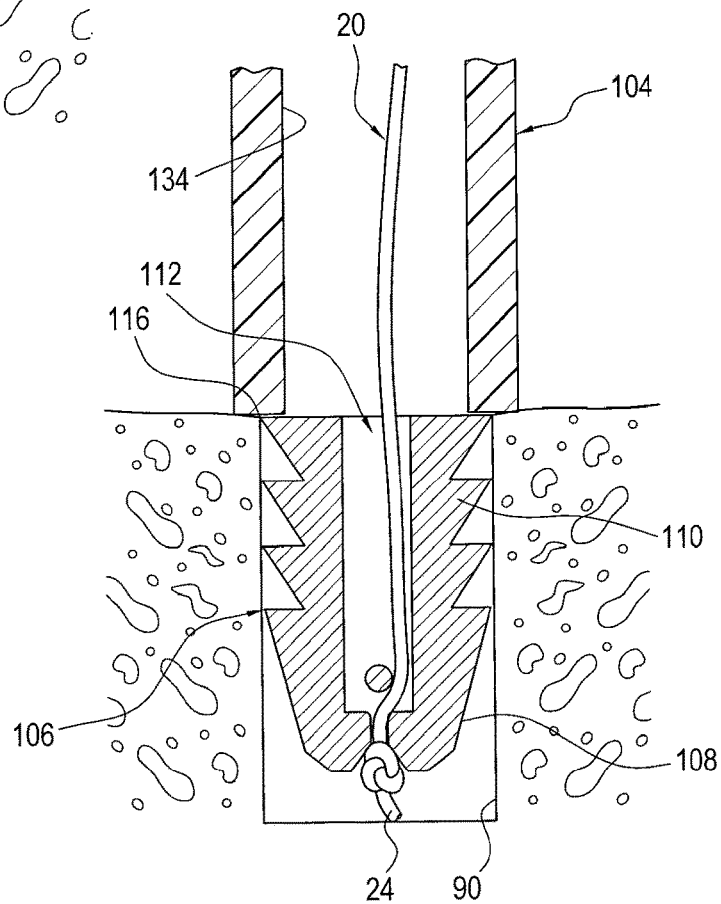

The one or more flexible strands 20 may be suture, suture tape, or any other flexible strand used for repairing tissue. In an exemplary embodiment, the one or more flexible strands 20 may be pre-loaded in the inner bore 112 of the fixation device 106 by coupling one end 22 of the flexible strand or strands 20 to the distal end 108 of the fixation device 106, such as via a knot 24, as seen in FIGS. 3a and 3b. Other known attachments may be used to couple the flexible strand or strands 20 to the fixation device 106. The other end 24 of the flexible strand or strands 20 can remain free for use in the surgical repair. A shuttling device (not shown) may also be coupled to the strand or strands 20 to assist with the repair.

Figure 2A:
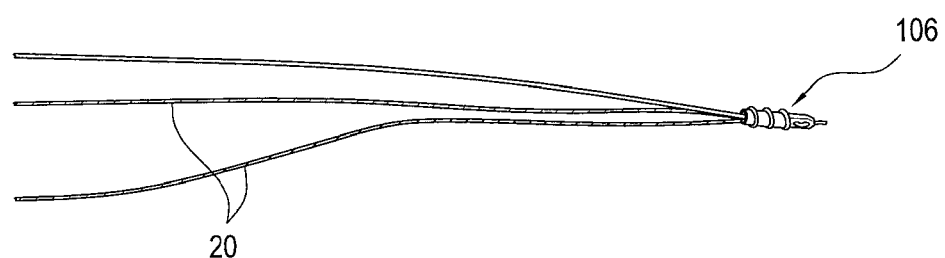
FIG. 2*a* is a plan view of a fixation device of the surgical inserter assembly illustrated in FIG. 1, showing the fixation device pre-loaded with a flexible strand.
Figure 2B:
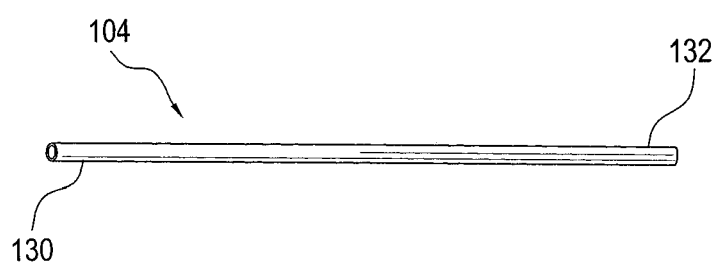
FIG. 2*b* is a plan view of an outer protector tube of the surgical inserter assembly illustrated in FIG. 1.
Figure 2C:
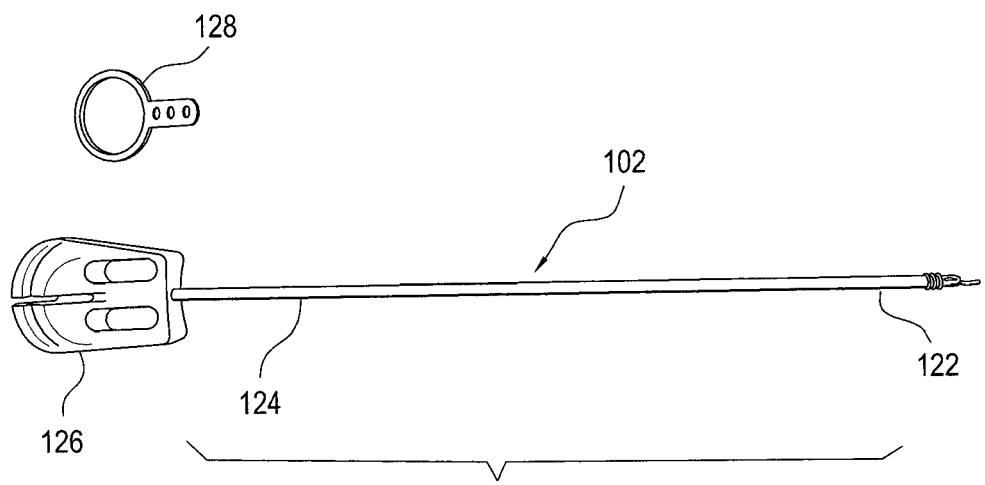
FIG. 2*c* is a plan view of an inserter of the surgical inserter assembly illustrated in FIG. 1, showing the pre-loaded fixation device coupled to the inserter.
Figure 2D:
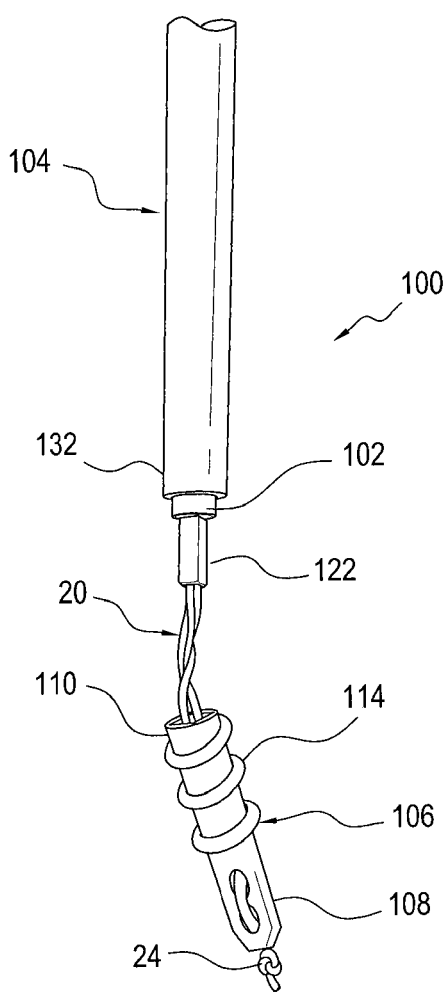
FIG. 2*d* is an enlarged partial plan view of the end of the surgical inserter assembly illustrated in FIG. 1, showing the fixation device.

The inserter 102 may comprise a cannulated shaft 120 that has a fixation device engagement end 122 configured to engage the proximal end 110 of the fixation device 106 and an opposite handle end 124 associated with a handle 126 of the inserter assembly 100, as best seen in FIGS. 2c and 2d. The cannulated shaft 120 is configured to receive the one or more flexible strands 20 therein. The one or more flexible strands 20 may be inserted into the fixation device engagement end 122 and through the cannulated shaft 120.

The outer protector tube 104 can be configured to fit over and slidably receive the cannulated shaft 120 of the inserter 102 and may be positioned between the handle 126 and the proximal end 110 of the fixation device 106, as seen in FIG. 1. Preferably, the protector tube 104 is generally axially fixed in place with respect to the longitudinal axis of the assembly 100, such that the ends 130 and 132 of the tube 104 either abut or nearly abut the handle 126 and the proximal end 110 of the fixation device prior to installation of the fixation device in the bone hole. Also, the inner diameter 134 of the protector tube 104 is preferably smaller than the outer diameter 116 of the proximal end 110 of the fixation device, as seen in FIGS. 3a and 3b, such that no portion of the fixation device 106 is received inside of the protector tube 104. The protector tube 104 is configured and sized such that the inserter 102 can be removed from the outer protector tube 102 after anchoring the fixation device 106 in the bone hole 90, while leaving the one or more flexible strands 20 extending through the outer protector tube 104, as seen in FIG. 3b. The length of the outer protector tube 120 is generally the same as the length of the cannulated shaft 120 of the inserter, so that the tube 104 substantially covers the entire length of the cannulated shaft 120. The protector tube 104 may be made of a plastic material or plastic composite, for example.

Figure 2E:
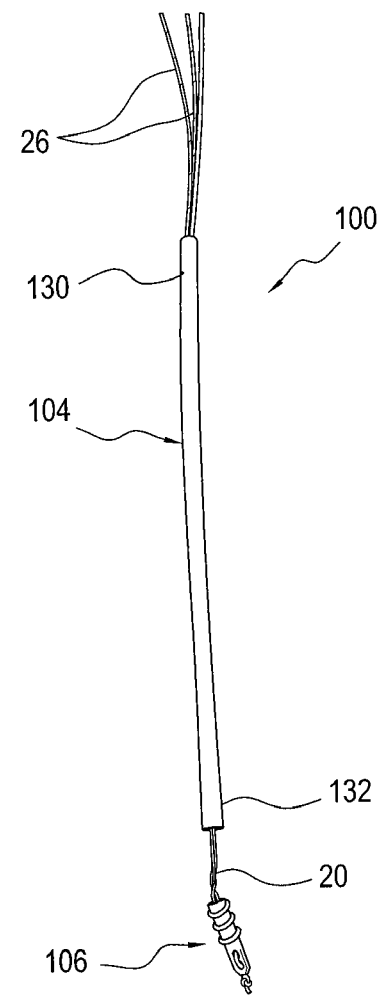
FIG. 2*e* is a plan view of the surgical inserter assembly illustrated in FIG. 1, showing the assembly with the inserter removed.

In preparation for a surgical tissue repair, the inserter assembly 100 is assembled by positioning the protector tube 104 over cannulated shaft 120 of the inserter 102 and engaging the end 122 of the cannulated shaft 120 with the proximal end 110 of the fixation device 106. The fixation device 106 is pre-loaded with the strand 20, as seen in FIG. 2a, and the strand 20 is inserted into and through the cannulated shaft 120 of the inserter via its end 122, as seen in FIG. 2e. Preferably, the protector tube 104 is first positioned over the cannulated shaft 120 of the inserter prior to threading the strands 20 through the cannulated shaft 120.

Once assembled, the inserter assembly 100 is ready for the tissue repair procedure. After drilling the hole 90 into the bone, the fixation device 106 is installed therein using the inserter 102, as seen in FIG. 3a, to rotationally thread the fixation device in the bone hole 90. In this position, the protector tube 104 rests above the bone hole 90 such that no portion of the tube 104 enters the bone hole 90. As seen in FIGS. 3a and 3b, the outer diameter of the outer protector tube 104 is larger than the inner diameter of the bone hole 90. The protector tube 104 is supported by the surrounding tissue and skin where the fixation device 106 is inserted. The fixation device 106 is configured to close off the bone hole 90 when inserted therein. After installing the fixation device 106 in the bone hole 90, the inserter 102 is disengaged from the proximal end 110 of the fixation device 106 and removed from the protector tube 104. The inserter 102 may be removed by, for example, removing an O-ring 128 of the inserter assembly's handle 126 and unwinding the strands 20.

When the inserter 102 is removed, the protector tube 104 stays in place and remains stationary with the one or more repair strands 20 are left inside of the protector tube 104, as seen in FIG. 3b, to protect the strands 20 during additional surgical steps post installation of the fixation device 106. Such additional surgical steps may include, for example, repositioning an arthroscopic camera into the sub-acromial space and debride the surrounding tissue. The surgeon may clear out the surrounding tissue with a radio frequency wand or a tissue shaver. The protector tube 104 protects the strands 20 from being damaged by the instruments used for tissue debridement.

It should be understood that Willis such as "lateral," "medial," "distal," "proximal," "superior," and "inferior" are used above consistent with the way those terms are used in the art. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A method of using a surgical inserter assembly, the method comprising:
   positioning an outer protector tube over a cannulated shaft of an inserter;
   engaging an end of the cannulated shaft of the inserter with a fixation device that is pre-loaded with at least one flexible strand;
   rotating the inserter into a bone hole, tunnel, or other crevice while the outer protector tube rests above the bone hole, tunnel, or other crevice, to install the fixation device in the bone hole, tunnel, or other crevice;

after installing the fixation device in the bone hole, tunnel, or other crevice, disengaging the inserter from the fixation device and removing the inserter from the outer protector tube, while leaving the fixation device in the bone hole, tunnel, or other crevice, leaving the outer protector tube in place resting above the bone hole, tunnel, or other crevice, and leaving the at least one flexible strand inside of the outer protector tube; and clearing tissue surrounding an outside of the outer protector tube while the outer protector tube remains in place and the at least one flexible strand remains protected inside of the outer protector tube.

2. The method of claim 1, wherein the outer protector tube remains stationary while the inserter is removed from the outer protector tube.

3. The method of claim 1, wherein movement of the outer protector tube is restricted by a handle end of the inserter and a proximal end of the fixation device during installation of the fixation device.

4. The method of claim 1, further comprising extending the at least one flexible strand through the cannulated shaft of the inserter after positioning the outer protector tube over the cannulated shaft and before installation of the fixation device.

5. The method of claim 4, wherein the at least one flexible strand extends through the outer protector tube after the inserter is removed from the outer protector tube.

6. The method of claim 4, wherein once the at least one flexible strand extends through the cannulated shaft of the inserter, the outer protector tube is fixed in place between a handle of the inserter and a proximal end of the fixation device.

7. The method of claim 6, further comprising removing the handle of the inserter before removing the inserter from the outer protector tube.

8. The method of claim 1, wherein installing the fixation device further comprises threading the fixation device into the bone hole, tunnel, or other crevice to anchor the fixation device into the bone hole, tunnel, or other crevice.

9. The method of claim 1, further comprising pre-drilling the bone hole, tunnel, or other crevice prior to installing the fixation device.

10. The method of claim 1, wherein an inner diameter of the outer protector tube is less than an outer diameter of a proximal end of the fixation device, such that no portion of the outer protector tube is inserted into the bone hole, tunnel, or other crevice.

11. The method of claim 1, wherein the inserter is configured to rotate independent of the outer protector tube.

12. The method of claim 1, wherein the outer protector tube is made of plastic or a plastic composite.

13. The method of claim 1, wherein the fixation device does not pass through the outer protector tube.

14. A method of tissue repair, the method comprising:
providing a pre-assembled surgical inserter assembly comprising:
an inserter comprising a handle and a cannulated shaft,
a fixation device having a proximal end that engages the cannulated shaft of the inserter,
at least one flexible strand captured by a distal end of the fixation device and extending through the cannulated shaft of the inserter, and
an outer protector tube that receives the cannulated shaft of the inserter, the outer protector tube having a first end that abuts the handle of the inserter and a second end that is opposite the first end and that abuts the proximal end of the fixation device such that the outer protector tube is axially fixed between the handle and the fixation device;
rotating the inserter independent of the outer protector tube into a bone hole, tunnel, or other crevice while the outer protector tube rests above the bone hole, tunnel, or other crevice, to install the fixation device in the bone hole, tunnel, or other crevice;
after installing the fixation device in the bone hole, tunnel, or other crevice, disengaging the inserter from the fixation device and removing the inserter from the outer protector tube, while leaving the fixation device in the bone hole, tunnel, or other crevice, leaving the outer protector tube in place resting above the bone hole, tunnel, or other crevice, and leaving the at least one flexible strand inside of the outer protector tube; and
clearing tissue surrounding an outside of the outer protector tube while the outer protector tube remains in place and the at least one flexible strand remains protected inside of the outer protector tube.

15. The method of claim 14, wherein the outer protector tube remains stationary while the inserter is removed from the outer protector tube.

16. The method of claim 14, further comprising pre-drilling the bone hole, tunnel, or other crevice prior to installing the fixation device.

17. The method of claim 14, further comprising removing the handle of the inserter before removing the inserter from the outer protector tube.

18. The method of claim 14, wherein installing the fixation device further comprises threading the fixation device into the bone hole, tunnel, or other crevice to anchor the fixation device into the bone hole, tunnel, or other crevice.

19. The method of claim 14, wherein an inner diameter of the outer protector tube is less than an outer diameter of the proximal end of the fixation device, such that no portion of the outer protector tube is inserted into the bone hole, tunnel, or other crevice.

20. The method of claim 14, wherein the outer protector tube is made of plastic or a plastic composite.

* * * * *